(12) United States Patent
Nelson

(10) Patent No.: US 11,819,612 B2
(45) Date of Patent: Nov. 21, 2023

(54) RESPIRATORY MASK SYSTEM

(71) Applicant: Fisher & Paykel Healthcare Limited, Auckland (NZ)

(72) Inventor: Grant Leigh Nelson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 448 days.

(21) Appl. No.: 17/066,309

(22) Filed: Oct. 8, 2020

(65) Prior Publication Data
US 2021/0106780 A1 Apr. 15, 2021

Related U.S. Application Data

(60) Provisional application No. 62/913,331, filed on Oct. 10, 2019.

(51) Int. Cl.
*A61M 16/06* (2006.01)

(52) U.S. Cl.
CPC .... *A61M 16/0616* (2014.02); *A61M 16/0683* (2013.01)

(58) Field of Classification Search
CPC ......... A61M 16/06–0694; A62B 18/02; A62B 18/025; A62B 23/02; A62B 23/025
See application file for complete search history.

(56) References Cited

U.S. PATENT DOCUMENTS

| | | |
|---|---|---|
| 5,921,239 A | 7/1999 | McCall et al. |
| 6,269,814 B1 | 8/2001 | Blaszczykiewicz et al. |
| 6,851,428 B2 | 2/2005 | Dennis |
| 7,533,906 B2 | 5/2009 | Luettgen et al. |
| 7,931,025 B2 | 4/2011 | Eaton et al. |
| 8,261,417 B2 | 9/2012 | Yoshiguchi |
| 8,596,274 B2 | 12/2013 | Hieber et al. |
| 8,752,254 B2 | 6/2014 | Perner |
| 9,272,109 B2 | 3/2016 | Rothermel et al. |
| 10,603,456 B2 | 3/2020 | Bearne et al. |
| 10,828,449 B2 | 11/2020 | Higgins et al. |

(Continued)

FOREIGN PATENT DOCUMENTS

| | | |
|---|---|---|
| AU | 2014202233 A1 | 5/2014 |
| CA | 2852636 C | 5/2013 |

(Continued)

OTHER PUBLICATIONS

UK Intellectual Property Office, Combined Search and Examination Report under Sections 17 and 18(3); Application No. GB2019664.8, dated Jan. 19, 2021, in 5 pages.

(Continued)

*Primary Examiner* — Valerie L Woodward
(74) *Attorney, Agent, or Firm* — Knobbe Martens Olson & Bear LLP

(57) ABSTRACT

A respiratory mask includes a housing and a cushion or seal that seals on a user's face in use. An upper portion of the seal that is disposed on a user's nasal bridge in use can roll toward and/or over the outer surface of the housing to form a rolling bridge feature that adjusts to different nose sizes. As the rolling bridge rolls, an apex of the seal moves away from the user's face to adjust to larger nose sizes. The apex does not move downward and can move upward relative to a location of the apex in a neutral position of the seal.

20 Claims, 15 Drawing Sheets

(56) References Cited

U.S. PATENT DOCUMENTS

| | | |
|---|---|---|
| 2003/0051732 A1 | 3/2003 | Smith et al. |
| 2003/0127101 A1 | 7/2003 | Carnell |
| 2004/0182398 A1 | 9/2004 | Sprinkle et al. |
| 2005/0155603 A1 | 7/2005 | Frerichs et al. |
| 2006/0196511 A1 | 9/2006 | Lau et al. |
| 2007/0044804 A1 | 3/2007 | Matula, Jr. et al. |
| 2007/0125385 A1 | 6/2007 | Ho et al. |
| 2007/0163600 A1 | 7/2007 | Hoffman |
| 2007/0209663 A1 | 9/2007 | Marque et al. |
| 2008/0178875 A1 | 7/2008 | Henry |
| 2009/0038619 A1 | 2/2009 | Ho et al. |
| 2009/0044808 A1 | 2/2009 | Guney et al. |
| 2010/0229868 A1 | 9/2010 | Rummery et al. |
| 2011/0005524 A1 | 1/2011 | Veliss |
| 2012/0103340 A1 | 5/2012 | Chu et al. |
| 2012/0222680 A1 | 9/2012 | Eves et al. |
| 2012/0234326 A1 | 9/2012 | Mazzone et al. |
| 2012/0285452 A1 | 11/2012 | Amirav et al. |
| 2013/0186404 A1 | 7/2013 | Chien |
| 2013/0228173 A1 | 9/2013 | Busch |
| 2014/0096774 A1 | 4/2014 | Olsen et al. |
| 2014/0174446 A1 | 6/2014 | Prentice et al. |
| 2014/0311494 A1 | 10/2014 | Gibson et al. |
| 2015/0090266 A1* | 4/2015 | Melidis .............. A61M 16/06 128/205.25 |
| 2015/0246198 A1* | 9/2015 | Bearne ............. A61M 16/0611 128/205.25 |
| 2016/0151596 A1* | 6/2016 | Slight ............. A61M 16/0622 128/207.18 |
| 2017/0266403 A1* | 9/2017 | Prentice .......... A61M 16/0622 |
| 2018/0185598 A1* | 7/2018 | Olsen .............. A61M 16/0611 |
| 2020/0230341 A1 | 7/2020 | Bearne et al. |

FOREIGN PATENT DOCUMENTS

| | | |
|---|---|---|
| CN | 101450239 | 6/2009 |
| EP | 3848078 | 7/2012 |
| EP | 2 281 596 | 10/2012 |
| EP | 2 668 971 | 12/2013 |
| EP | 2 818 194 | 12/2014 |
| EP | 2758113 | 10/2016 |
| EP | 3372268 | 9/2018 |
| EP | 3175877 | 5/2019 |
| EP | 3578219 | 12/2020 |
| GB | 2343722 | 5/2002 |
| GB | 2393126 | 11/2004 |
| GB | 2426711 | 12/2006 |
| JP | 2011-512967 | 4/2011 |
| JP | 2014-517735 | 7/2014 |
| WO | WO 02/047749 | 6/2002 |
| WO | WO 03/090827 | 11/2003 |
| WO | WO 04/021960 | 3/2004 |
| WO | WO 04/022146 | 3/2004 |
| WO | WO 04/041341 | 5/2004 |
| WO | WO 04/071565 | 8/2004 |
| WO | WO 05/123166 | 12/2005 |
| WO | WO 06/130903 | 12/2006 |
| WO | WO 08/040050 | 4/2008 |
| WO | WO 09/026627 | 3/2009 |
| WO | WO 09/108995 | 9/2009 |
| WO | WO 10/066004 | 6/2010 |
| WO | WO 10/071453 | 6/2010 |
| WO | WO 10/131189 | 11/2010 |
| WO | WO 10/135785 | 12/2010 |
| WO | WO 11/060479 | 5/2011 |
| WO | WO 12/045127 | 4/2012 |
| WO | WO 2012/140514 | 10/2012 |
| WO | WO 13/006899 | 1/2013 |
| WO | WO 13/064950 | 5/2013 |
| WO | WO 2013/066195 | 5/2013 |
| WO | WO2013066195 | 5/2013 |
| WO | WO 2014/062070 | 4/2014 |
| WO | WO 14/129913 | 8/2014 |

OTHER PUBLICATIONS

Japanese Patent Office, Pre-Appeal Review, Application No. JP 2017-511715, dated Dec. 17, 2020, in 7 pages.

* cited by examiner

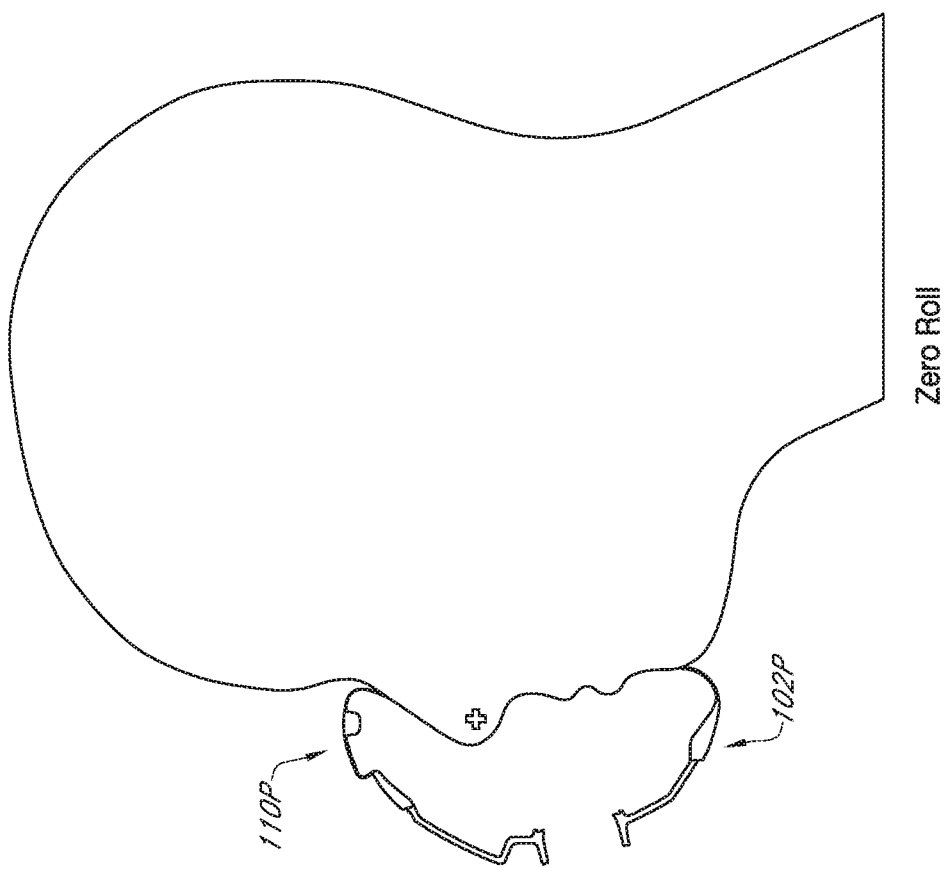

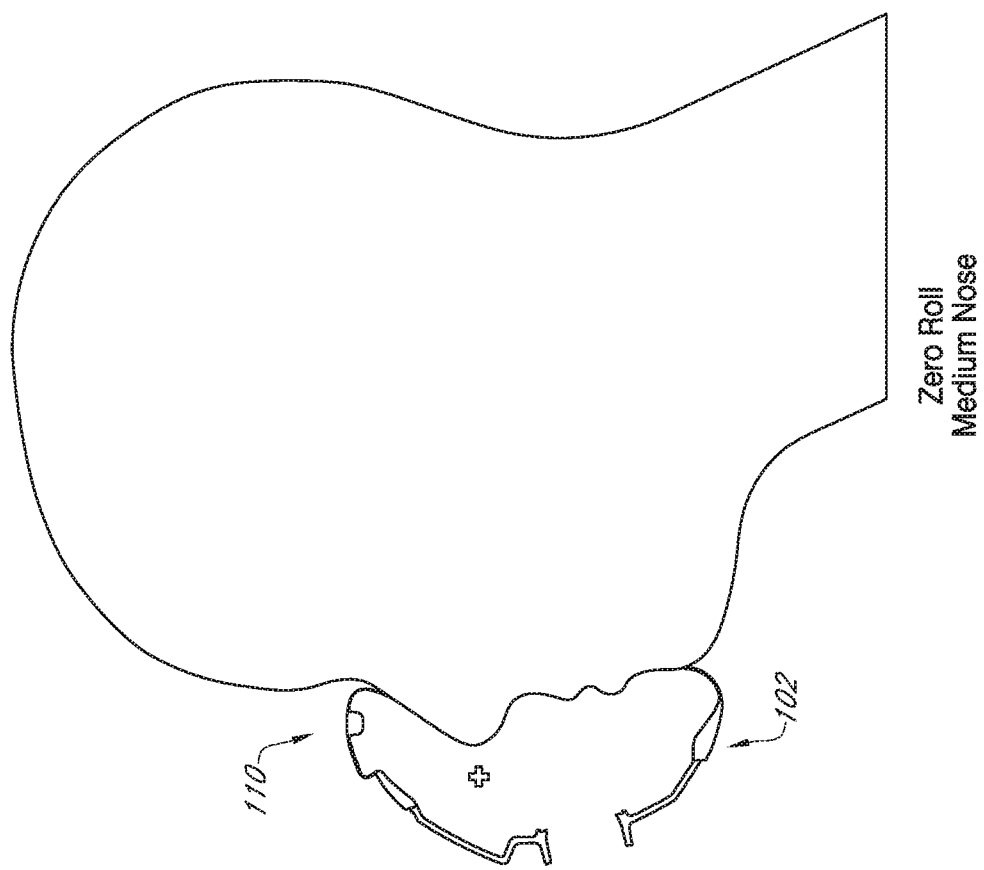

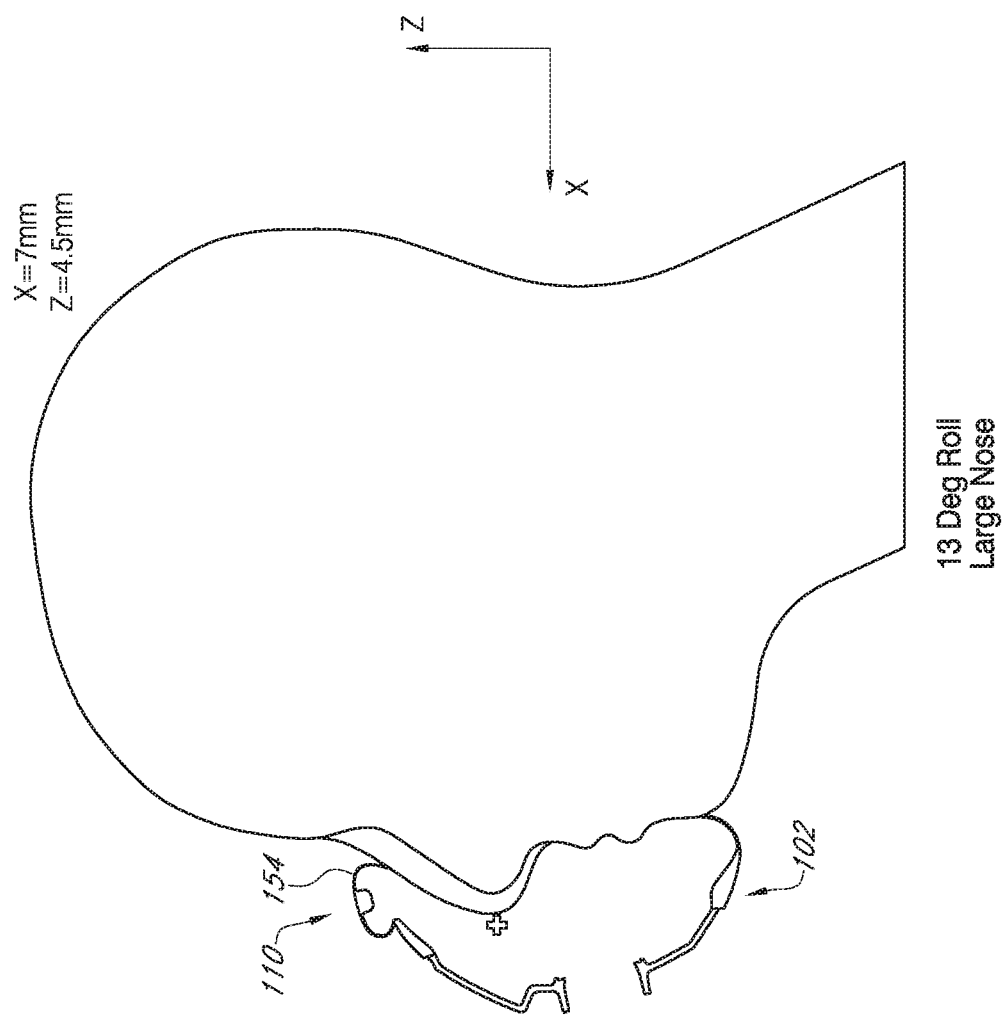

RESPIRATORY MASK SYSTEM

BACKGROUND

Field

The present disclosure generally relates to a respiratory mask for the delivery of respiratory therapy to a patient. More particularly, certain aspects of the present disclosure relate to a respiratory mask having a seal with an improved pivotal nasal portion.

Description of Related Art

Respiratory masks are used to provide respiratory therapy to the airways of a person suffering from any of a number of respiratory illnesses or conditions. Such therapies may include but are not limited to positive airway pressure (PAP) therapy, such as continuous positive airway pressure (CPAP), and non-invasive ventilation (NIV) therapy.

Respiratory masks typically include a patient interface and a headgear, wherein the patient interface is configured to deliver the supply of positive air pressure to the patient's airway via a seal or cushion that forms an airtight seal in or around the patient's nose and/or mouth. In some interface types, the seal or cushion overlies the bridge of the user's nose. The seal or cushion is held in place on the patient's face by the headgear. In order to maintain an airtight seal, the headgear should provide support to the patient interface such that it is held in a stable position relative to the patient's face during use. In order to sufficiently reduce leakage, the headgear typically is tightened, which can result in an elevated pressure being exerted on a bridge of a user's nose. In other words, as the headgear is tightened, the seal or cushion typically applies an increasing pressure on the bridge of the nose. Because the bridge of the nose is a particularly sensitive area, this pressure can be a source of discomfort and, in some circumstances, can lead to pressure sores over time.

SUMMARY

The systems and devices described herein have innovative aspects, no single one of which is indispensable or solely responsible for their desirable attributes. Without limiting the scope of the claims, some of the advantageous features will now be summarized.

An aspect of the present disclosure involves a full-face respiratory mask having a housing and a seal. The seal is coupled to the housing and defines a contact surface configured to contact a user's face in use. The seal is configured to surround the mouth and a portion of the nose of the user in use. The seal includes an upper portion and a lower portion. The upper portion includes an apex point located on the contact surface and on a vertically-oriented center line of the mask. The upper portion is configured for pivotal movement relative to the lower portion about a pivot point within a range of motion from an undeflected position to a deflected position. The upper portion includes a rolling portion configured for rolling movement toward the housing and over an outer surface of the mask in response to the pivotal movement of the upper portion from the undeflected position towards the deflected position. The pivot point is positioned in front of the apex point over an entirety of the range of motion with the mask in an in-use orientation.

In some configurations, in response to the rolling movement of the rolling portion toward the housing, the apex point moves upward and away from the user.

In some configurations, a change in location of the apex point in an upward direction is equal to or greater than one-half of a change in location of the apex point in a forward direction from the undeflected position to the deflected position.

In some configurations, the apex point is located at least 5 mm upward and at least 10 mm further away from the user in the deflected position relative to a location of the apex point in the undeflected position.

In some configurations, with the upper portion pivoted about 13° toward the housing from the undeflected position, the apex point is located about 4.5 mm upward and about 7 mm further away from the user relative to a location of the apex point in the undeflected position.

In some configurations, with the upper portion pivoted about 21° from the undeflected position, the apex point is located about 7 mm upward and about 12 mm further away from the user relative to the location of the apex point in the undeflected position.

In some configurations, with the upper portion pivoted 13° toward the housing from the undeflected position, the apex point is located at least 4.5 mm upward and at least 7 mm further away from the user relative to a location of the apex point in the undeflected position.

In some configurations, with the upper portion pivoted 21° from the undeflected position, the apex point is located at least 7 mm upward and at least 12 mm further away from the user relative to the location of the apex point in the undeflected position.

In some configurations, the pivotal movement of the range of motion is at least about 20°.

In some configurations, at least a portion of the upper portion is more flexible than an entirety of the lower portion.

In some configurations, at least a portion of the upper portion is thinner than an entirety of the lower portion.

An aspect of the present disclosure involves a respiratory mask including a housing and a seal. The seal is coupled to the housing and defines a contact surface configured to contact a user's face in use. The seal includes an upper portion and a lower portion. The upper portion includes an apex point located on the contact surface and on a vertically-oriented center line of the mask. The upper portion configured for pivotal movement relative to the lower portion about a pivot point. The upper portion includes a rolling portion configured to roll from an undeflected position to a deflected position. With the mask in an in-use orientation, and with the upper portion pivoted to a maximum roll angle, the apex point is located at least 5 mm upward and at least 10 mm further away from the user relative to a location of the apex point in the undeflected position.

In some configurations, the maximum roll angle is at least about 21°.

In some configurations, at least a portion of the upper portion is more flexible than an entirety of the lower portion.

In some configurations, at least a portion of the upper portion is thinner than an entirety of the lower portion.

In some configurations, the pivot point is positioned in front of the apex point over an entire range of motion of the upper portion.

In some configurations, a change in location of the apex point in an upward direction is equal to or greater than one-half of a change in location of the apex point in a forward direction from the undeflected position to the deflected position.

In some configurations, with the upper portion pivoted 13° toward the housing from the undeflected position, the apex point is located at least 4.5 mm upward and at least 7 mm further away from the user relative to a location of the apex point in the undeflected position.

In some configurations, with the upper portion pivoted to the maximum roll angle, the apex point is located at least 7 mm upward and at least 12 mm further away from the user relative to the location of the apex point in the undeflected position.

An aspect of the present disclosure involves a respiratory mask having a housing and a seal. The seal is coupled to the housing and defines a contact surface configured to contact a user's face in use. The seal includes an upper portion and a lower portion. The upper portion includes an apex point located on the contact surface and on a vertically-oriented center line of the mask. The upper portion is configured for pivotal movement relative to the lower portion about a pivot point. The upper portion is configured to roll from an undeflected position to a deflected position. With the mask in an in-use orientation, a change in location of the apex point in an upward direction is equal to or greater than one-half of a change in location of the apex point in a forward direction from the undeflected position to the deflected position.

In some configurations, the respiratory mask is a full-face mask in which the seal is configured to create a seal around the mouth and nares of the user in use.

In some configurations, the apex point is located at least 5 mm upward and at least 10 mm further away from the user in the deflected position relative to a location of the apex point in the undeflected position.

In some configurations, the deflected position is at least 13° from the undeflected position.

In some configurations, the deflected position is at least 20° from the undeflected position.

In some configurations, the deflected position is about 21° from the undeflected position.

In some configurations, with the upper portion pivoted 13° from the undeflected position, the apex point is located at least 4.5 mm upward and at least 7 mm further away from the user relative to a location of the apex point in the undeflected position.

In some configurations, with the upper portion pivoted 21° from the undeflected position, the apex point is located at least 7 mm upward and at least 12 mm further away from the user relative to the location of the apex point in the undeflected position.

In some configurations, the change in location of the apex point in the upward direction is at least 3 mm, 4.5 mm or 7 mm from the undeflected position to the deflected position.

In some configurations, the pivot point remains in front of the apex point at all positions between the undeflected position and the deflected position.

An aspect of the present disclosure involves a full-face respiratory mask including a housing and a seal. The seal is coupled to the housing and defines a contact surface configured to contact a user's face in use. The seal is configured to surround the mouth and a portion of the nose of the user in use. The seal includes an upper portion and a lower portion. The upper portion includes an apex point located on the contact surface and on a vertical center line of the mask. The upper portion is configured for pivotal movement relative to the lower portion about a pivot point within a range of motion from an undeflected position to a deflected position. The upper portion comprises a rolling portion configured for rolling movement toward the housing and over an outer surface of the mask in response to the pivotal movement of the upper portion from the undeflected position towards the deflected position. The apex point moves at least 10 mm in a forward direction and does not move in a downward direction between the undeflected position and the deflected position with the mask in an in-use orientation.

In some configurations, the pivot point is positioned in front of the apex point over an entirety of the range of motion.

In some configurations, in response to the rolling movement of the rolling portion toward the housing, the apex point moves upward.

In some configurations, a change in location of the apex point in the upward direction is equal to or greater than one-half of a change in location of the apex point in the forward direction from the undeflected position to the deflected position.

In some configurations, the apex point is located at least 5 mm upward and at least 10 mm further away from the user in the deflected position relative to a location of the apex point in the undeflected position.

In some configurations, with the upper portion pivoted about 13° toward the housing from the undeflected position, the apex point is located about 4.5 mm upward and about 7 mm further away from the user relative to a location of the apex point in the undeflected position.

In some configurations, with the upper portion pivoted about 21° from the undeflected position, the apex point is located about 7 mm upward and about 12 mm further away from the user relative to the location of the apex point in the undeflected position.

In some configurations, with the upper portion pivoted 13° toward the housing from the undeflected position, the apex point is located at least 4.5 mm upward and at least 7 mm further away from the user relative to a location of the apex point in the undeflected position.

In some configurations, with the upper portion pivoted 21° from the undeflected position, the apex point is located at least 7 mm upward and at least 12 mm further away from the user relative to the location of the apex point in the undeflected position.

In some configurations, the pivotal movement of the range of motion is at least about 20°.

In some configurations, at least a portion of the upper portion is more flexible than an entirety of the lower portion.

In some configurations, at least a portion of the upper portion is thinner than an entirety of the lower portion.

An aspect of the present disclosure involves a respiratory mask including a housing and a seal. The seal is coupled to the housing and defines a contact surface configured to contact a user's face in use. The seal includes an upper portion and a lower portion. The upper portion includes an apex point located on the contact surface and on a vertical center line of the mask. The upper portion is configured for pivotal movement relative to the lower portion about a pivot point within a range of motion from an undeflected position to a deflected position. A horizontal distance between the pivot point and the apex point is at least about 10 mm with the mask in an in-use orientation and the upper portion in the undeflected position.

In some configurations, the horizontal distance between the pivot point and the apex point is at least about 15 mm.

In some configurations, the horizontal distance between the pivot point and the apex point is at least about 20 mm.

In some configurations, the horizontal distance between the pivot point and the apex point is between about 10-40 mm.

In some configurations, the horizontal distance between the pivot point and the apex point is between about 20-30 mm.

In some configurations, the horizontal distance between the pivot point and the apex point is between about 22-28 mm.

In some configurations, the horizontal distance between the pivot point and the apex point is between about 24-26 mm.

In some configurations, the apex point moves at least 10 mm in a forward direction and does not move in a downward direction between the undeflected position and the deflected position with the mask in an in-use orientation.

In some configurations, the pivot point is positioned in front of the apex point over an entirety of the range of motion.

In some configurations, the upper portion comprises a rolling portion configured for rolling movement toward the housing and over an outer surface of the mask in response to the pivotal movement of the upper portion from the undeflected position towards the deflected position.

In some configurations, in response to the rolling movement of the rolling portion toward the housing, the apex point moves upward.

In some configurations, a change in location of the apex point in the upward direction is equal to or greater than one-half of a change in location of the apex point in the forward direction from the undeflected position to the deflected position.

In some configurations, the apex point is located at least 5 mm upward and at least 10 mm further away from the user in the deflected position relative to a location of the apex point in the undeflected position.

In some configurations, with the upper portion pivoted about 13° toward the housing from the undeflected position, the apex point is located about 4.5 mm upward and about 7 mm further away from the user relative to a location of the apex point in the undeflected position.

In some configurations, with the upper portion pivoted about 21° from the undeflected position, the apex point is located about 7 mm upward and about 12 mm further away from the user relative to the location of the apex point in the undeflected position.

In some configurations, with the upper portion pivoted 13° toward the housing from the undeflected position, the apex point is located at least 4.5 mm upward and at least 7 mm further away from the user relative to a location of the apex point in the undeflected position.

In some configurations, with the upper portion pivoted 21° from the undeflected position, the apex point is located at least 7 mm upward and at least 12 mm further away from the user relative to the location of the apex point in the undeflected position.

In some configurations, the pivotal movement of the range of motion is at least about 20°.

In some configurations, at least a portion of the upper portion is more flexible than an entirety of the lower portion.

In some configurations, at least a portion of the upper portion is thinner than an entirety of the lower portion.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 6B schematically illustrates the prior art mask of FIG. 6A with the seal in a neutral position.

FIG. 8B schematically illustrates the mask of FIG. 8A with the seal in a neutral position.

FIG. 8C schematically illustrates the mask of FIG. 8A with the seal in an intermediate rolled position.

DETAILED DESCRIPTION

Figure 1:
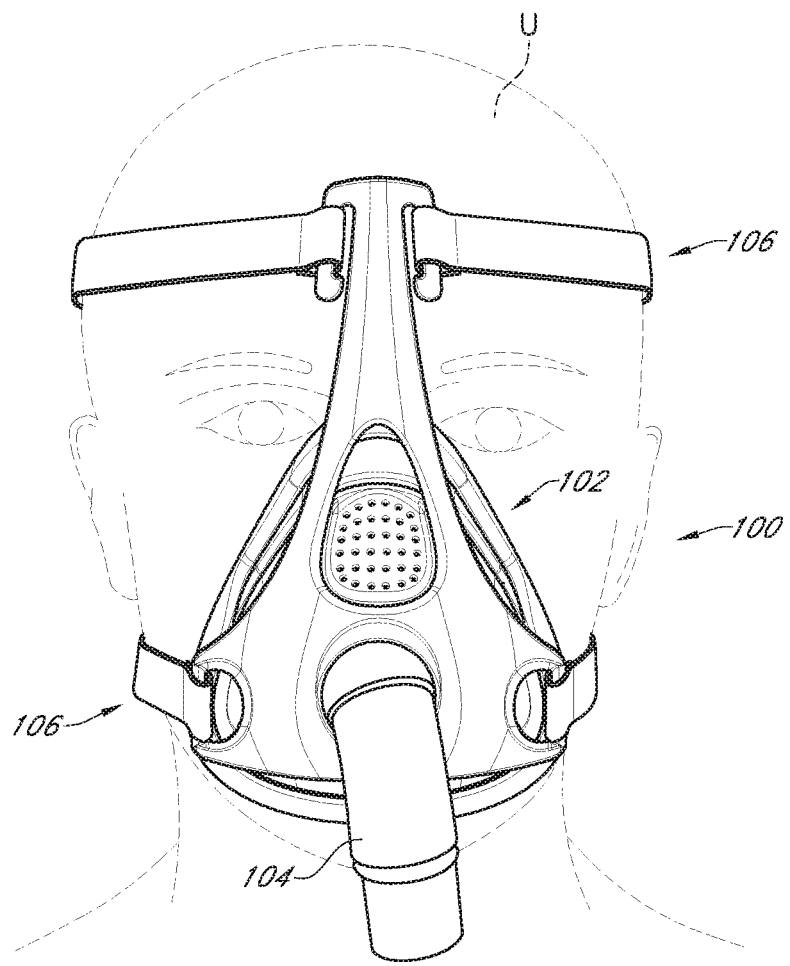
FIG. 1 illustrates a front view of a user wearing a mask assembly.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" may refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. In the context of a patient interface, a forward direction is away from the user and a rearward direction is toward the user relative to an orientation of the patient interface properly positioned on a user with the user's head in an upright position. In addition, a right side and a left side is from the user's perspective with the patient interface properly positioned on a user with the user's head in an upright position. Moreover, terms such as "first," "second," "third," and so on may be used to describe separate components. Such terminology may include the words specifically mentioned above, derivatives thereof, and words of similar import.

Figure 2:
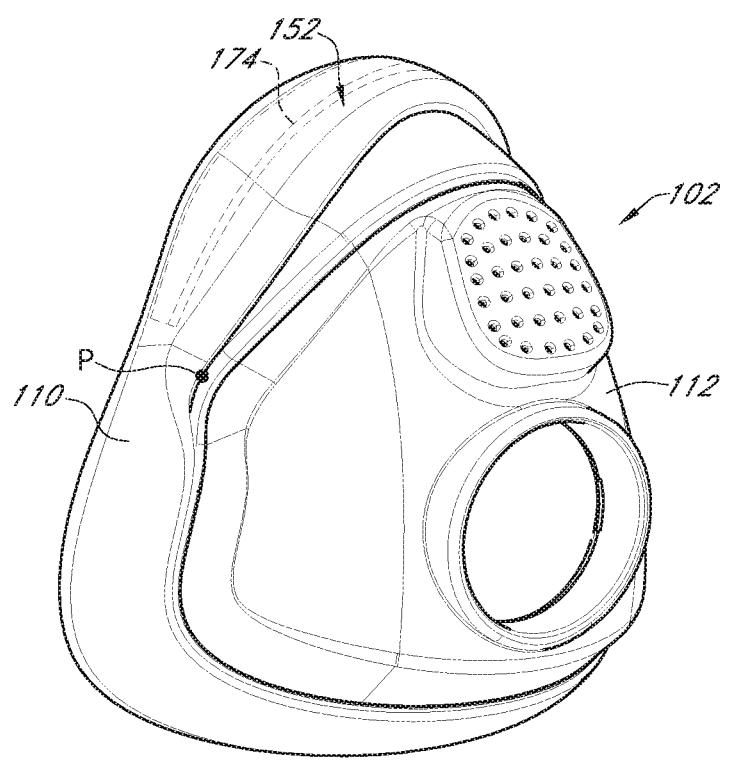
FIG. 2 illustrates a front perspective view of an interface or mask of the mask assembly of FIG. 1.
Figure 3:
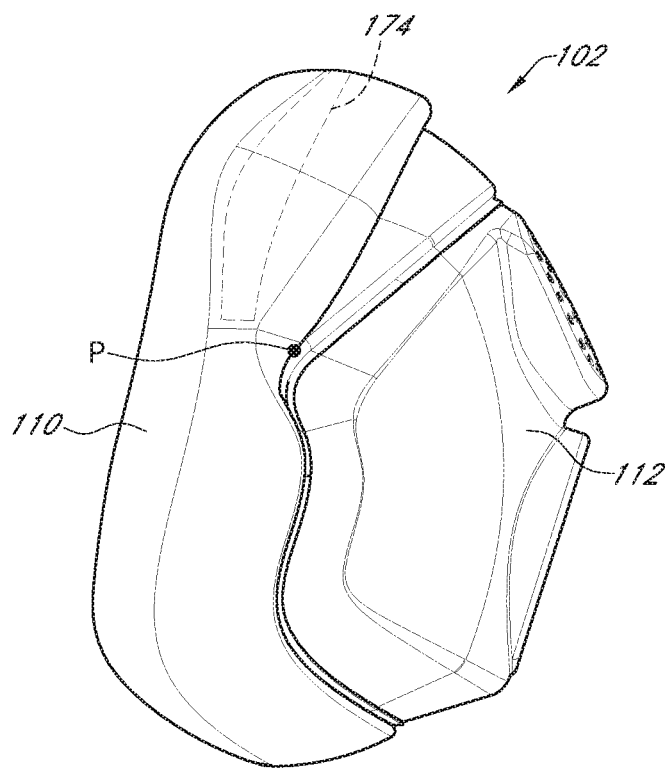
FIG. 3 illustrates a side view of the mask of FIG. 2.

FIG. 1 illustrates an example embodiment of a mask assembly 100 including an interface in the form of a mask 102, a gas supply tube connector 104, and a headgear assembly 106 disposed on a user U. As shown in FIGS. 2 and 3, the mask 102 includes a seal 110 and a frame or housing 112. In some configurations, the frame or housing 112 directly or indirectly couples to the headgear assembly 106 and/or connector 104. The connector 104 couples to a gas supply conduit in use to deliver breathing gases to the mask 102 to be delivered to the airways of the user. The frame or housing 112 can be relatively more rigid, stiffer, or more inflexible than the seal 110 and can provide structural support to the mask seal 110. In some embodiments, the seal 110 is made of silicone or a similar elastomer material. In some embodiments, the frame or housing 112 is made of polycarbonate or a similar plastic material.

In some embodiments, the mask 102 is a full-face mask and the seal 110 is configured to surround the mouth and at least a portion of the nose of the user in use. The seal 110 can include a contact surface 130 that contacts and forms a sufficient seal with the face of the user to allow for the desired therapy under normal use conditions. The contact surface 130 surrounds the mouth and the nares of the nose of the user during use. In other embodiments, the mask 102 can be a nasal mask, and the seal 110 can be configured to surround at least a portion of the nose of the user in use. For example, in such an arrangement, a contact surface 130 of the seal 110 could surround the nares of the nose of the user in use.

Figure 4:
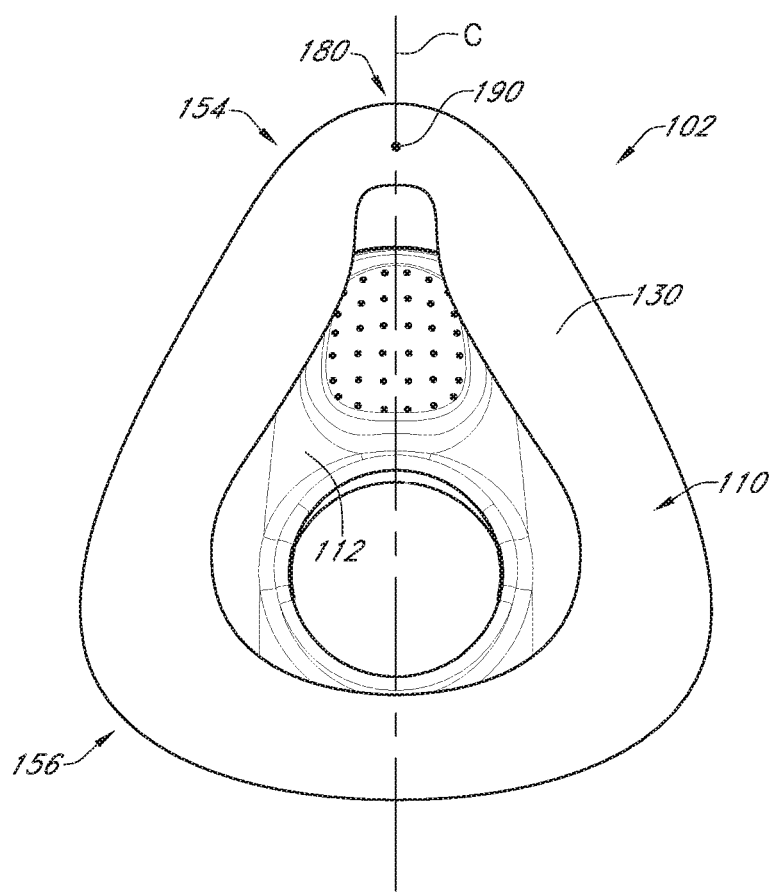
FIG. 4 illustrates a rear view of the mask of FIG. 3.

The illustrated seal 110 has an upper portion 154 and a lower portion 156. The upper portion 154 of the seal 110 extends over a nasal region, e.g., the nasal bridge, of the user in use. The upper portion 154 includes an apex 180 positioned in proximity to the nose of the user when in use. The apex 180 can be defined as a top, an uppermost point or portion and/or an angular summit of the seal 110. The upper portion 154 also includes a nasal contact point or an apex point 190, which is a point along a vertical midline or center line C (FIG. 4) of the seal 110 on the contact surface 130 that contacts the user's nose in use. The center line C lies within a vertical center plane that bisects the mask 102 or seal 110 into two lateral (left and right) sides or halves. Thus, the apex point 190 can be said to lie within the vertical center plane of the mask 102. The center line C can be a tangent line or touch a point on the contact surface 130 in each of the upper portion 154 and the lower portion 156. The nasal contact or apex point 190 is used as a reference point herein to illustrate certain characteristics of movement of the upper portion 154 of the seal 110 relative to the lower portion 156 of the seal 110. The nasal contact or apex point 190 can be located at any desired location along a vertical midline or center line C of the seal 110 on the contact surface 130 at the apex 180. For example, the nasal contact or apex point 190 can be located at a vertical center point of the contact surface 130 along the vertical midline or center line C of the apex 180 of the seal 110. However, the nasal contact or apex point 190 can be located elsewhere along the vertical midline or center line C of the apex 180 to allow for comparisons between different positions of the upper portion 154 relative to the lower portion 156. Although the nasal contact or apex point 190 is used herein for convenience, other reference points can be used to illustrate movement of the upper portion 154 of the seal 110. Such alternative reference points can be located at any desired location on or relative to the upper portion 154 of the seal 110 or a portion of the seal that moves relative to another portion of the seal.

Figure 5:
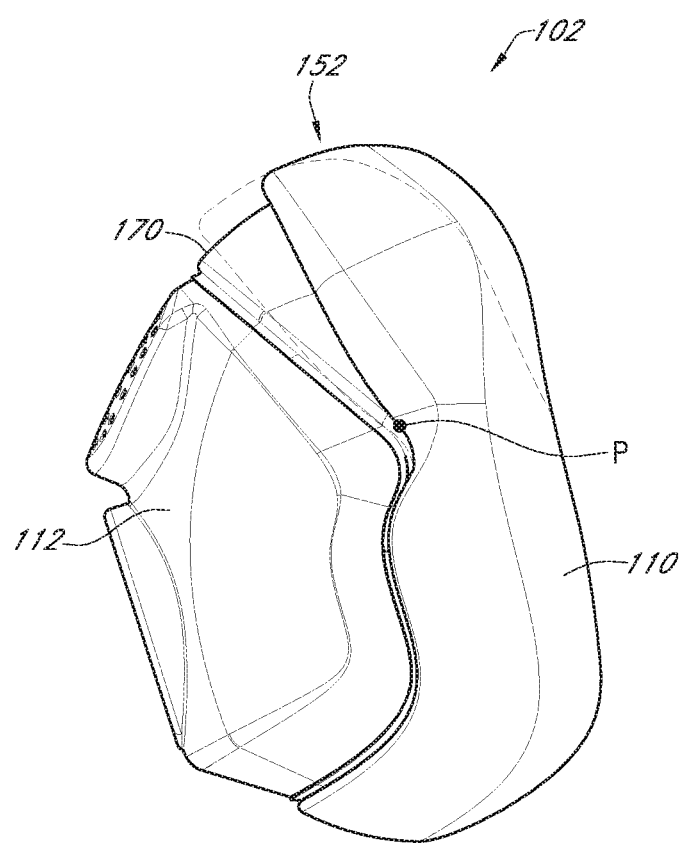
FIG. 5 illustrates a side view of the mask of FIGS. 3 and 4 showing operation of a rolling bridge feature.

The upper portion 154 of the seal 110 is configured to pivot or hinge relative to the lower portion 156 of the seal 110 about a hinge axis H to allow pivotal movement of the upper portion 154 in a forward direction (a direction away from the face of the user U or toward the housing 112). As shown in FIG. 2, the hinge axis H extends laterally through the mask 102. In the illustrated arrangement, a rolling portion 152 of the upper portion 154 of the seal 110 is configured to roll in response to the pivotal movement of the upper portion 154. As shown by the dashed lines in FIG. 5, the rolling portion 152 is designed to roll toward the front of the mask 102 (i.e., in a direction away from the user). As a result, an inflection point between a first or upper wall and a second or lower wall of the rolling portion 152 moves along the rolling portion 152 and lengths of the upper wall and lower wall vary during the rolling movement. In some configurations, a lower wall does not exist in a neutral position of the rolling portion 152 and is created upon rolling movement of the rolling portion 152. In some configurations, the rolling portion 152 rolls over and/or onto an outer surface 170 of the mask 102, which can be another portion of the seal 110 and/or the housing 112. The rolling portion 152 can be referred to herein as a rolling bridge. The rolling bridge 152 can advantageously allow the seal 110 to adapt to a range of user facial features and sizes. At least a portion of the upper portion 154 can be more flexible or less stiff or rigid, e.g., thinner, than a portion or an entirety of the lower portion 156, which can help allow or encourage the upper portion 154 to roll.

The upper portion 154 can include a reinforcement portion, which can be in the form of a reinforcement band 174, that is more rigid or stiffer than adjacent or surrounding portions or the remainder of the upper portion 154. In the illustrated embodiment, the band 174 is made of the same material as a portion or the remainder of the seal 110 but is thicker than at least the rolling bridge 152. In some configurations, the band 174 is thicker than the remainder of the seal 110. The band 174 can provide enhanced structure and reinforce the upper portion 154 and/or can act as a stop for forward rolling movement of the rolling bridge 152. In the illustrated embodiment, the band 174 extends laterally across the apex 180 of the upper portion 154 of the seal 110 and partially down the sides of the seal 110. In the illustrated arrangement, the band 174 protrudes inwardly from an inner surface of the upper portion 154. However, in other embodiments, the band 174 can protrude outwardly from an outer surface of the upper portion 154.

The ends of the band 174 can terminate at or near the hinge axis H. As shown in FIG. 3, in the illustrated arrangement, the ends of the band 174 terminate above the hinge axis H. The hinge axis H extends through pivot points P on either side of the mask 100 that are positioned at or below lower ends of the band 174. In the illustrated arrangement, the pivot points P are positioned along a line extending along the front or leading edge of the band 174 (i.e. the edge of the band positioned away from the user in use and/or the leading edge as the upper portion 154 rolls onto the housing 112). In some embodiments, the pivot points P are defined by changes in thickness of the seal 110. However, other arrangements for creating desirable pivot points P can also be used. Moreover, the pivot points P may not be distinct points, but can be a region or area, preferably a small region or area, about which movement of the upper portion 154 occurs. In some configurations, the pivot points P may move along with movement of the upper portion 154. Thus, in such configurations, movement of the upper portion 154 may occur about a moving instantaneous pivot point P. An average pivot point P may be defined by the path of movement of such a moving pivot point P.

Figure 6A:
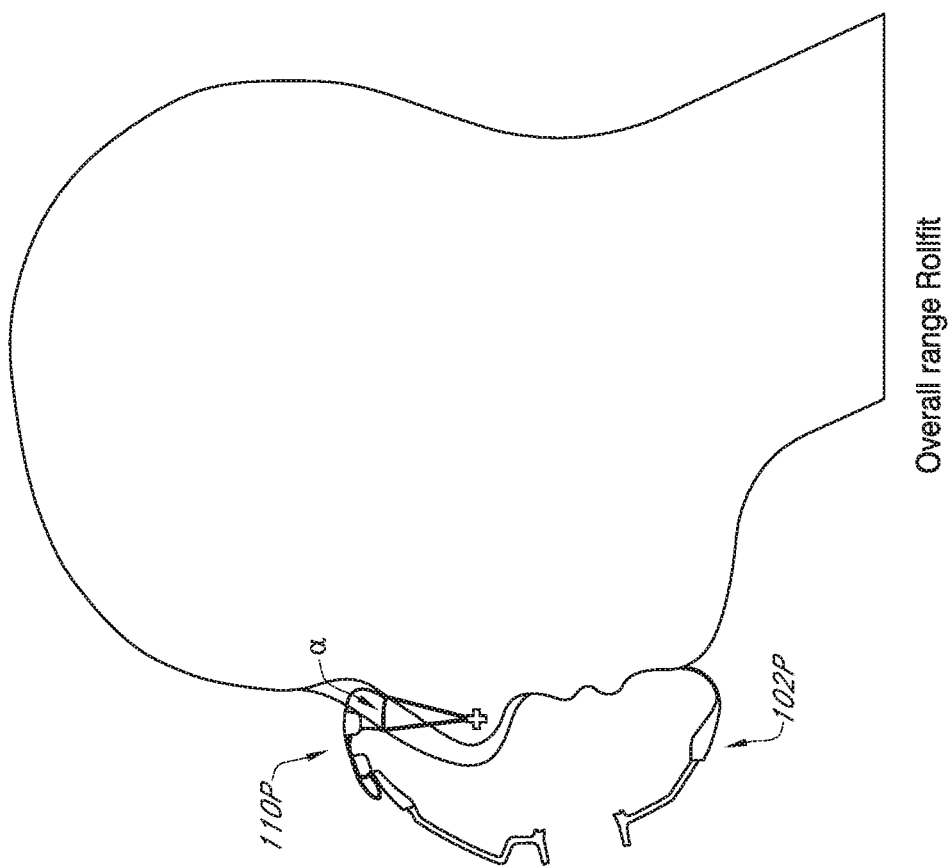
FIG. 6A schematically illustrates a roll profile of a prior art seal having a rolling bridge feature.
Figure 6C:
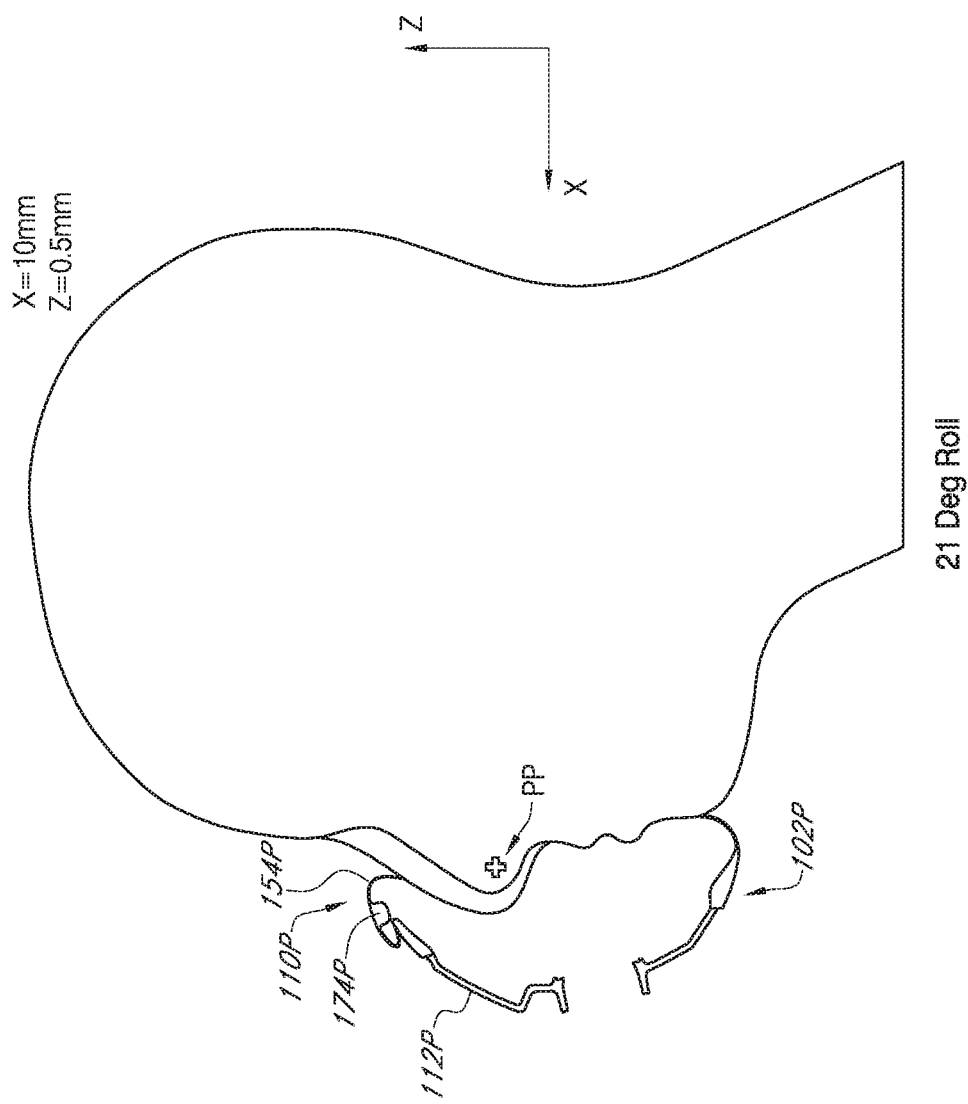
FIG. 6C schematically illustrates the prior art mask of FIGS. 6A and 6B with the seal in a maximum roll position.

For the sake of comparison, FIGS. 6A-6C illustrate movement of a rolling bridge 152P of a prior art mask 102P that allows the seal 110P to adjust and adapt to different facial geometries. The prior art mask 102P can be similar to the mask 102 of the present application except as discussed herein. Accordingly, similar features are identified by the same reference characters with a "P" added to the reference characters of the prior art mask 102P. FIG. 6A illustrates an overall range of the rolling bridge 152P. FIG. 6B shows the seal 110P in a neutral or undeflected position with no or zero roll. FIG. 6C shows the seal 110P in a fully deflected position with maximum roll to accommodate a larger profile nasal bridge. The upper portion 154P can also adjust to any rolled position between the neutral position and the maximum roll position. As the upper portion 154P rolls from the neutral position toward, over and/or onto the outer surface 170P of the mask 102P, the apex 180P, band 174P and nasal contact point 190P move away from and downward or inferiorly relative to the patient's face.

As described above, FIG. 6A shows the maximum roll position of FIG. 6C superimposed on the neutral position of FIG. 6B. A roll angle α of the upper portion 154P can be defined as the angle between a first line extending from the hinge axis H or pivot point PP to the apex 180P in the neutral position and a second line extending from the hinge axis H or pivot point PP to the apex 180P in the rolled position, as shown in FIG. 6A. In the illustrated prior art mask 102P, the roll angle α has a range of 21°. In other words, the roll angle α is 21° in the maximum roll position of the illustrated embodiment. In the illustrated prior art mask 102P, when the upper portion 154P rolls from the neutral position to the maximum roll position, the apex 180P moves 10 mm away from the patient's face in the x direction and 0.5 mm downward or inferiorly in the z direction as labeled in FIG. 6C.

Figure 7:
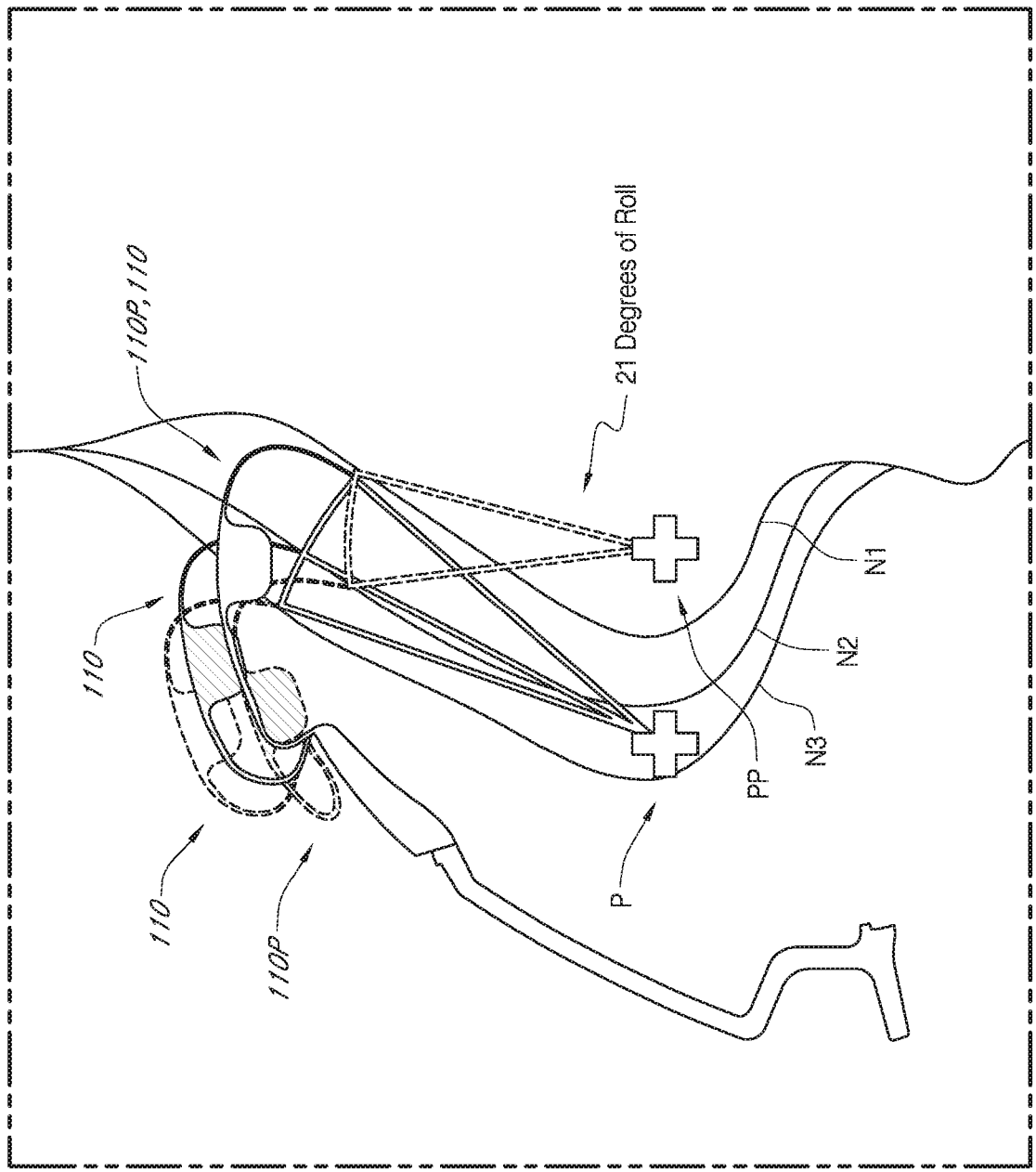
FIG. 7 schematically illustrates a roll profile of the seal of an example embodiment of a mask superimposed on the roll profile of the prior art mask of FIG. 6A.
Figure 8A:
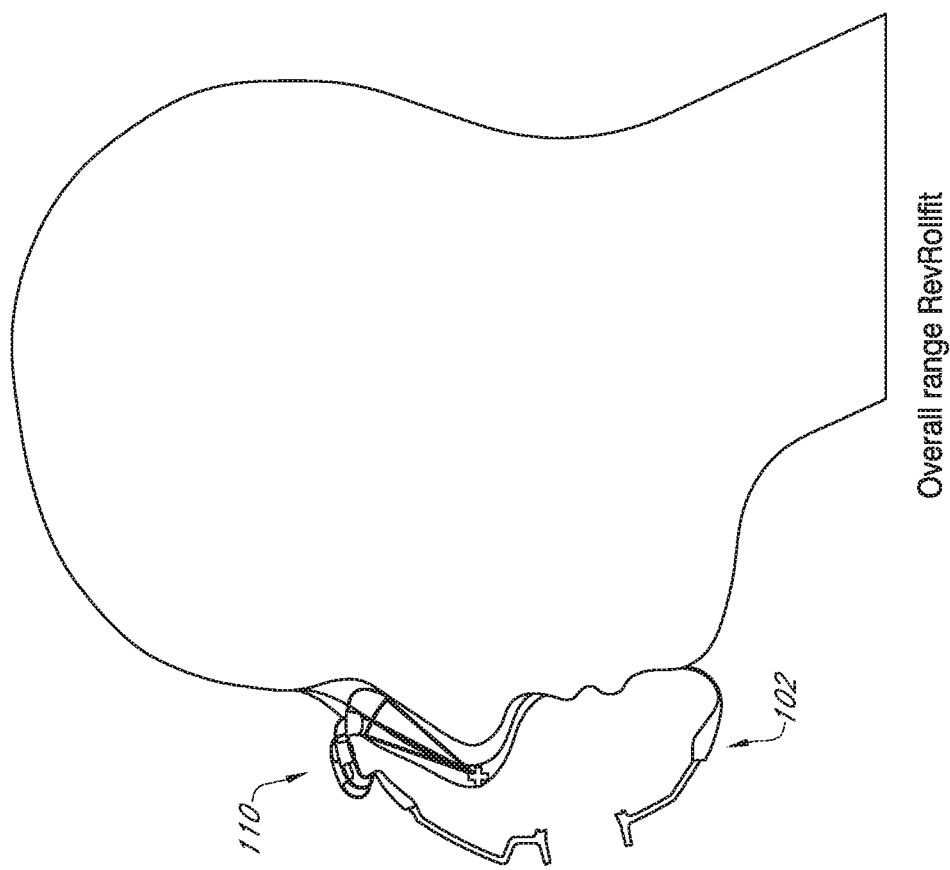
FIG. 8A schematically illustrates the roll profile of the seal of the example embodiment of the mask of FIG. 7.

FIG. 8A shows a roll profile or overall range of roll and size accommodation of an example embodiment of a mask, such as the mask 100 of FIGS. 1-5. As described above, the mask 100 includes a seal 110 having an improved rolling bridge 152. FIG. 7 shows the roll profile of the seal 110 superimposed on the roll profile of the prior art seal 110P of FIGS. 6A-6C. As illustrated, the pivot point P of the seal 110 is located distally of or away from the patient's face relative to the pivot point PP of the seal 110P. That is, the location of the pivot point PP of the prior art seal 110P of FIGS. 6A-6C is indicated by PP in FIG. 7, and the relocated pivot point of the inventive seal 110P is indicated by P. As shown, the relocated pivot point P is positioned vertically below or inferior of the rolling bridge 152. In the illustrated arrangement, the relocated pivot point P is positioned farther away from the patient's face than the apex point 190 of the upper portion 154 throughout a majority or an entirety of the range of motion of the rolling bridge 152. The pivot point P can be relocated relative to the pivot point PP of the prior art mask 100P by, for example, shifting the location of regions of different stiffness and boundaries between such regions in the upper portion 154. For example, the band 174 may be shifted such that the ends or lower portions of the band 174 are positioned more forward toward the housing or away from the user's face relative to the band 174P.

The roll angle α of the seal 110 can have a range of at least about 20° or at least about 21°. In the illustrated embodiment, the roll angle α of the seal 110 has a range of 21° similar to the prior art seal 110P of FIGS. 6A-6C. However, the relocated pivot point P allows the seal 110 to accommodate and adapt to a wider range of nose sizes as shown. In FIG. 7, the seals 110P, 110 are each shown in their respective neutral positions to accommodate a "medium" sized nose N1. FIG. 7 also shows the seals 110P, 110 in a first deflected or rolled position to accommodate a "large" sized nose N2. The first deflected position of the seal 110P is the maximum roll position for the seal 110P. That is, the seal 110P can only accommodate the "large" sized nose N2 at a maximum amount of deflection. FIG. 7 further shows the improved seal 110 in a second deflected position, which is its maximum deflected position or maximum roll position. In the maximum roll position, the seal 110 is able to accommodate an "extra-large" sized nose N3. The difference between the nasal outline of the "large" sized nose N2 and the nasal outline of the "extra-large" sized nose N3 illustrates the additional size range that seal 110 can accommodate compared to seal 110P.

In some configurations, the rolling bridge 152 of the seal 110 does not move in a downward direction throughout its range of motion. In some configurations, the rolling bridge 152 of the illustrated seal 110 moves in an upward direction as it progresses through its range of movement, as illustrated in FIG. 7. As a result, the height or vertical dimension of the seal 110 increases as the rolling bridge 152 deflects, which moves the contact surface 130 upward on the user's nose relative to the prior art seal 110P. Such an arrangement advantageously enhances the ability of the seal 110 to accommodate a larger range of face and/or nose sizes relative to the prior art seal 110P. In some configurations the contact surface 130, because it moves upwardly as the rolling bridge 152 deflects, may advantageously contact a variety of increasingly large nose sizes on a substantially similar position, which provides a more uniform fitment between users with varying nose sizes.

FIG. 8A illustrates an overall range of the rolling bridge 152 of the seal 110. As described above, as the upper portion 154 of seal 110 rolls from the neutral position, shown in FIG. 8B, toward, over and/or onto the outer surface 170 of the mask 102, the seal 110, e.g., the apex 180, band 174, and/or nasal contact point 190, moves in a forward direction away from the user's face and does not move to a position that is downward from or lower than the neutral position. In some configurations, in addition to moving in a forward direction, the seal 110, e.g., the apex 180, the band 174 and/or the nasal contact point 190 moves in an upward direction or superiorly relative to the patient's face.

Figure 9A:
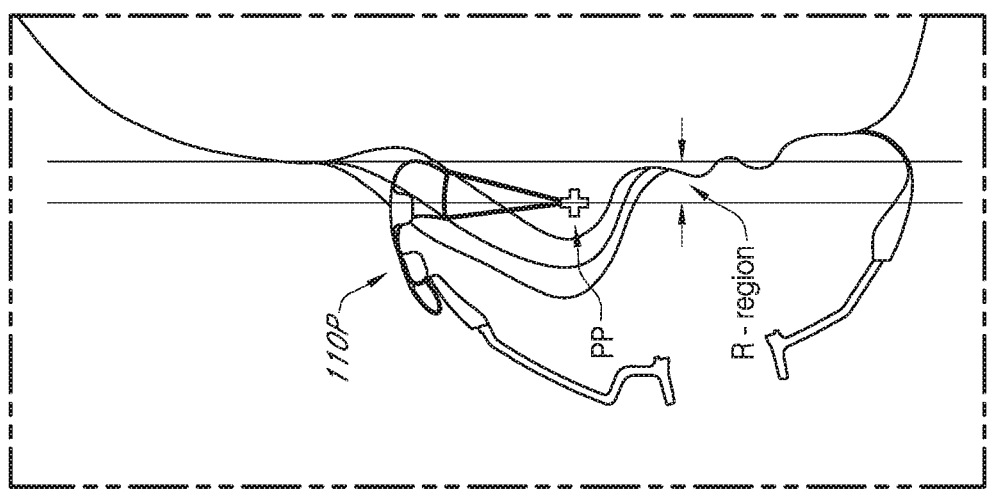
FIGS. 9A and 9B schematically illustrate the roll profiles of the masks of FIGS. 6A and 8A, respectively.
Figure 9B:
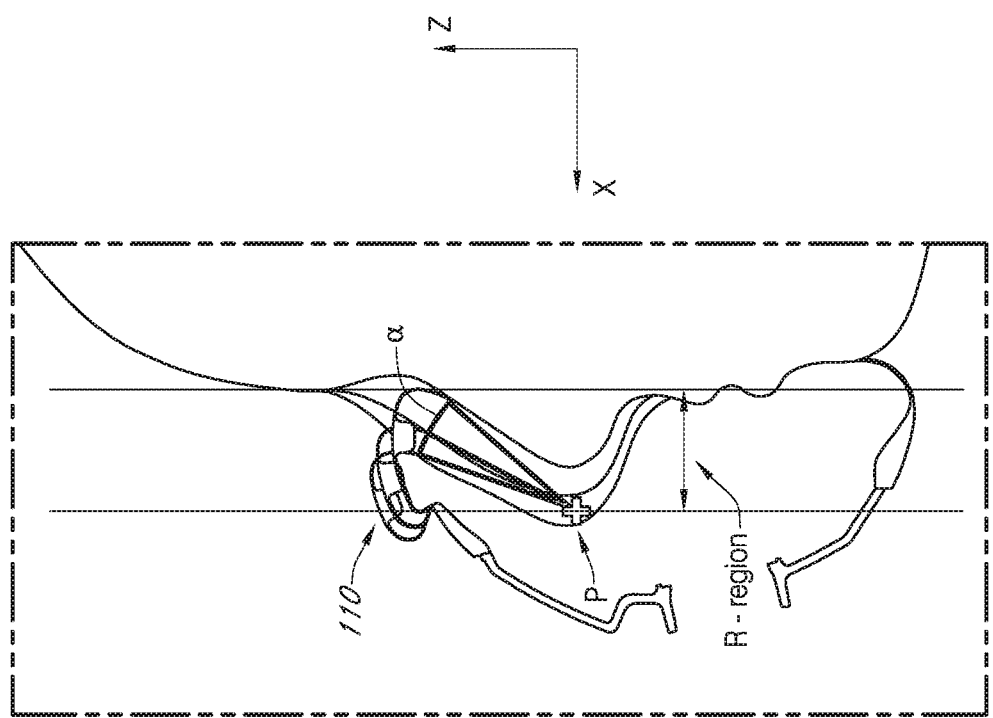

FIGS. 9A and 9B illustrate differences in direction of movement of the prior art seal 110P compared to movement of the inventive seal 110. As shown in FIG. 9A and described above, as the upper portion 154P of seal 110P rolls from the neutral position, the apex 180P, band 174P and nasal contact point 190P move away from and to a fully deflected position that is relatively downward or inferior to the neutral position. In contrast, as shown in FIG. 9B, as the upper portion 154 of seal 110 rolls from the neutral position, the upper portion 154 of the seal 110, e.g., the apex 180, band 174, and/or nasal contact point 190, moves away from and upward or superior relative to the neutral position. This allows the seal 110 to accommodate a larger size nose, indicated by outline N3 in FIG. 9B. The prior art seal 110P would require a larger angular range of movement to accommodate the same nose size N3 as the seal 110, which may not be possible or practical. Also, as described above, the upward movement of the upper portion 154 of the seal 110, e.g., the apex 180, band 174, and/or nasal contact point 190, increases a height or a vertical dimension of the seal 110 to better accommodate a larger range of facial and/or nose sizes.

Figure 8D:
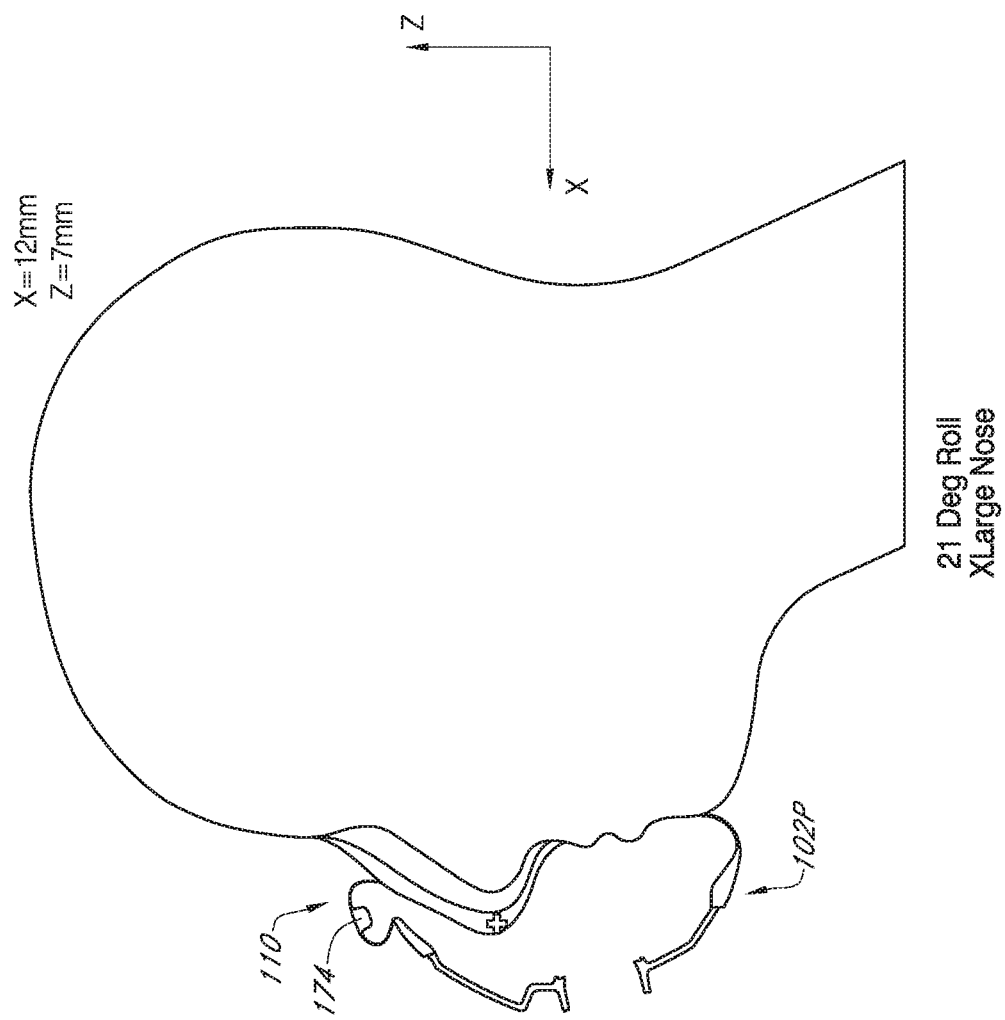
FIG. 8D schematically illustrates the mask of FIG. 8A with the seal in a maximum rolled position.

As shown in FIGS. 6C and 9A, when the seal 110P is in the maximum roll position, the apex or nasal contact point 190P of the upper portion 154P moves in front of (or farther away from the user's face than) the pivot point PP. In contrast, as shown in FIGS. 8D and 9B, when the seal 110 is in the maximum roll position, the apex or nasal contact point 190 of the upper portion 154 remains behind (or closer to the user's face than) the pivot point P. In other words, as illustrated in FIGS. 9A and 9B, if a region R is defined between a vertical line drawn through the top of the bridge of the user's nose at the location of the apex point or nasal contact point 190P, 190 with the seal 110P, 110 in a neutral position and a parallel line drawn through the pivot point PP, P, the nasal contact point 190 of the seal 110 remains within the region R throughout its range, whereas the nasal contact point 190P of the seal 110P moves outside of the region R as it adjusts to larger nose sizes. Thus, in at least some configurations, the pivot point P is positioned in front of the apex point or nasal contact point 190 over an entirety of the range of motion.

In some configurations of the seal 110 of the present disclosure, a horizontal dimension of the region R—which equals a horizontal distance between the apex or nasal contact point 190 and the pivot point P with the seal 110 in a neutral position—is at least about 10 mm, at least about 15 mm or at least about 20 mm. In some configurations, the horizontal dimension of the region R is between about 10-40 mm, between about 20-30 mm, between about 22-28 mm or between about 24-26 mm. Such a location of the pivot point P relative to the apex or nasal contact point 190 (or other reference point of the upper portion 154 of the seal 110) can provide advantageous forward and/or upward movement of the upper portion 154 or rolling bridge 152 of the seal 110 from the undeflected position to the deflected position.

As described above, in some configurations of the seal 110, the apex or nasal contact point 190 can move in a forward direction and an upward direction within the available range of movement of the rolling bridge 152 or upper portion 154. In some configurations, the upward movement is substantial relative to the forward movement. For example, a change in location of the apex point 190 in an upward direction can be equal to or greater than one-half of a change in location of the apex point 190 in a forward direction from the undeflected position to the deflected position. In other words, the upward movement is at least 50% of the forward movement or the forward movement is less than twice the upward movement. For example, the rolling bridge 152 or upper portion 154 can permit forward movement of the apex point 190 of at least 10 mm. Thus, in some configurations, the upward movement of the apex point 190 can be at least 5 mm when the forward movement is at least 10 mm. However, other arrangements are also possible. For example, if a large amount of forward travel is permitted, the upward movement may be less than 50% of the forward movement. Preferably, the absolute distance of upward movement is still substantial. In some configurations, the upward movement of the apex point 190 can be at least about 3 mm, 4.5 mm or 7 mm from the undeflected position to the deflected position of the rolling bridge 152 or upper portion 154.

The rolling bridge 152 or upper portion 154 of the seal 110 can be configured for any desired amount of adjustable movement within the available range or between the undeflected position and the deflected position. For example, the range of available movement may vary depending on the desired user population. Smaller user populations, such as when a relatively large number of seal sizes are provided, may only require a smaller range of movement, while larger populations, such as when a relatively small number of seal sizes are provided, may require a larger range of movement to accommodate a satisfactory portion of the population. In some configurations, the deflected position is 13° or at least 13° from the undeflected position. In some configurations, the deflected position is 20° or at least 20° from the undeflected position. In some configurations, the deflected position is 21° or at least 21° from the undeflected position.

In the embodiment of FIGS. 8A-8D and 9B, when the upper portion 154 of seal 110 is adjusted to the rolled position that accommodates the "large" sized nose N2 (which is the maximum size for seal 110P), the roll angle $\alpha$ is 13° or about 13°, and the upper portion 154 of the seal 110, e.g., the apex 180, band 174, and/or nasal contact point 190, moves at least 7 mm away from the patient's face in the x direction and at least 4.5 mm upward or superiorly in the z direction. In the illustrated arrangement, when the roll angle $\alpha$ is 13° or about 13°, the nasal contact point 190 moves 7 mm away from the patient's face in the x direction and 4.5 mm upward or superiorly in the z direction, as shown in FIG. 8C. When the upper portion 154 of seal 110 is adjusted to its maximum roll position, in some configurations the roll angle $\alpha$ is 21° or about 21°, and the upper portion 154 of the seal 110, e.g., the apex 180, band 174, and/or nasal contact point 190, moves at least 12 mm away from the patient's face in the x direction and at least 7 mm upward or superiorly in the z direction. In the illustrated arrangement, when the roll angle $\alpha$ is 21° or about 21°, the nasal contact point 190 moves 12 mm away from the patient's face in the x direction and 7 mm upward or superiorly in the z direction, as shown in FIG. 8D. The seal 110 with the improved rolling bridge 152 therefore accommodates the maximum nose size of seal 110 (i.e., "large" sized nose N2) with a smaller roll angle (i.e., 13° vs. 21°) and accommodates a larger nose size (i.e., "extra-large" sized nose N3) with the same maximum roll angle (i.e., 21°). Although the illustrated embodiment has a maximum roll angle of 21° and maximum displacement of 12 mm in the x direction and 7 mm in the z direction, other maximum roll angles and maximum displacements are also possible.

As described herein, an in-use orientation of the mask 102 (or prior art mask 102P) refers to the orientation of the mask 102 as properly fitted to a user with the user's head in an upright or vertical orientation. In an in-use orientation, the center line C of the mask 102 contacts the contact surface 130 in both the apex 180 and the lower portion 156 of the seal (e.g., chin for a full-face mask or upper lip for a nasal mask) with the seal 110 in a neutral position. The in-use orientation provides an initial orientation for the mask 102 and mask seal 110 for the purpose of describing movement of the upper portion 154 of the seal 110 relative to the lower portion 156. Descriptions of movement of the upper portion 154 or related reference points (e.g., the nasal contact or apex point 190, the apex 180 or the band 174) are relative to this initial orientation with the lower portion 156 of the seal 110 and the housing 112 remaining stationary. Thus, the descriptions of movement of the upper portion 154, whether as linear movement (e.g., x-direction or z-direction movement) or rotational movement (e.g., movement within a range of roll angles α), are in the context of theoretical movement, permissible movement or possible movement that allows the seal 110 to conform to different users—in contrast to actual movement when the mask 102 is applied to a specific user. For example, when applied to a specific user, the contact surface 130 will tend to remain stationary relative to the user while the housing 112 moves toward the user and the upper portion 154 of the seal 110 moves relative to the lower portion 156 of the seal 110 as the headgear 106 is tightened. The housing 112 may rotate relative to the face of the user in response to the relative movement of the upper portion 154 and the lower portion 156, which rotation may be equivalent to the rotation of the upper portion 154 described herein. However, for the sake of convenience, the description of the movement of the upper portion 154 herein assumes the lower portion 156 and the housing 112 remain stationary.

In some embodiments, the center line C is oriented in a vertical direction when the mask 102 is in the in-use orientation. In some embodiments, the center line C can be offset from the vertical direction when viewed from the side of the mask 102. In some cases, an upper portion of the center line C is located further forward (a direction away from the user's face) relative to a lower portion of the center line C. In other words, the point of contact with the user's nasal bridge is located in front of the point of contact with the lower portion 156 of the seal 110 along the center line C. In the illustrated arrangement, the center line C has an orientation between about 0-10 degrees, 0-5 degrees or 0-3 degrees relative to the vertical direction. As discussed above, non-zero angles of the center line C can have an upper portion of the center line C positioned forward of a lower portion of the center line C. However, in other configurations, it is possible for the upper portion of the center line C to be positioned rearward of the lower portion of the center line C.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

What is claimed is:

1. A respiratory mask comprising:
   a housing; and
   a seal coupled to the housing and defining a contact surface configured to contact a user's face in use, the seal comprising an upper portion and a lower portion, the upper portion comprising an apex point located on the contact surface and on a vertical center line of the mask, the upper portion configured for pivotal movement relative to the lower portion about a pivot point within a range of motion from an undeflected position to a deflected position;
   wherein a horizontal distance between the pivot point and the apex point is at least about 10 mm with the mask in an in-use orientation and the upper portion in the undeflected position.

2. The respiratory mask of claim 1, wherein the horizontal distance between the pivot point and the apex point is at least about 15 mm.

3. The respiratory mask of claim 1, wherein the horizontal distance between the pivot point and the apex point is at least about 20 mm.

4. The respiratory mask of claim 1, wherein the horizontal distance between the pivot point and the apex point is between about 10-40 mm.

5. The respiratory mask of claim 1, wherein the horizontal distance between the pivot point and the apex point is between about 20-30 mm.

6. The respiratory mask of claim 1, wherein the horizontal distance between the pivot point and the apex point is between about 22-28 mm.

7. The respiratory mask of claim 1, wherein the horizontal distance between the pivot point and the apex point is between about 24-26 mm.

8. The respiratory mask of claim 1, wherein the apex point moves at least 10 mm in a forward direction and does not move in a downward direction between the undeflected position and the deflected position with the mask in an in-use orientation.

9. The respiratory mask of claim 1, wherein the pivot point is positioned in front of the apex point over an entirety of the range of motion.

10. The respiratory mask of claim 1, wherein the upper portion comprises a rolling portion configured for rolling movement toward the housing and over an outer surface of the mask in response to the pivotal movement of the upper portion from the undeflected position towards the deflected position.

11. The respiratory mask of claim 10, wherein in response to the rolling movement of the rolling portion toward the housing, the apex point moves upward.

12. The respiratory mask of claim 1, wherein a change in location of the apex point in an upward direction is equal to or greater than one-half of a change in location of the apex point in a forward direction from the undeflected position to the deflected position.

13. The respiratory mask of claim 1, wherein the apex point is located at least 5 mm upward and at least 10 mm further away from the user in the deflected position relative to a location of the apex point in the undeflected position.

14. The respiratory mask of claim 1, wherein with the upper portion pivoted about 13° toward the housing from the undeflected position, the apex point is located about 4.5 mm upward and about 7 mm further away from the user relative to a location of the apex point in the undeflected position.

15. The respiratory mask of claim 1, wherein with the upper portion pivoted about 21° from the undeflected position, the apex point is located about 7 mm upward and about 12 mm further away from the user relative to the location of the apex point in the undeflected position.

16. The respiratory mask of claim 1, wherein with the upper portion pivoted 13° toward the housing from the undeflected position, the apex point is located at least 4.5 mm upward and at least 7 mm further away from the user relative to a location of the apex point in the undeflected position.

17. The respiratory mask of claim 1, wherein with the upper portion pivoted 21° from the undeflected position, the apex point is located at least 7 mm upward and at least 12 mm further away from the user relative to the location of the apex point in the undeflected position.

18. The respiratory mask of claim 1, wherein the pivotal movement of the range of motion is at least about 20°.

19. The respiratory mask of claim 1, wherein at least a portion of the upper portion is more flexible than an entirety of the lower portion.

20. The respiratory mask of claim 1, wherein at least a portion of the upper portion is thinner than an entirety of the lower portion.

* * * * *